United States Patent [19]

Davis

[11] Patent Number: 5,593,638
[45] Date of Patent: Jan. 14, 1997

[54] APPARATUS FOR ESTIMATING THE CHANGE IN AN ANALYTE FROM HEMOLYSIS IN A FLUID SAMPLE

[75] Inventor: Graham Davis, Plainsboro, N.J.

[73] Assignee: I-Stat Corporation, Princeton, N.J.

[21] Appl. No.: 359,595

[22] Filed: Dec. 20, 1994

Related U.S. Application Data

[62] Division of Ser. No. 131,527, Oct. 4, 1993, Pat. No. 5,416,026.

[51] Int. Cl.$^6$ .......................... G01N 21/01; G01N 31/22; G01N 33/20; G01N 33/72
[52] U.S. Cl. .......................... 422/56; 422/57; 422/58; 422/61; 422/68.1; 436/66; 436/73; 436/79; 436/169
[58] Field of Search .......................... 422/68.1, 81, 82.01, 422/82.02, 82.03, 82.05, 82.09, 56, 57, 58, 61; 436/66, 73, 79, 169, 175, 177

[56] References Cited

U.S. PATENT DOCUMENTS

| | | | |
|---|---|---|---|
| 3,539,300 | 11/1970 | Stone | 436/66 X |
| 3,552,925 | 1/1971 | Fetter | 432/56 X |
| 3,972,614 | 8/1976 | Johansen et al. | 356/36 |
| 4,057,394 | 11/1977 | Genshaw | 436/66 X |
| 4,263,512 | 4/1981 | Sagusa et al. | 250/373 |
| 4,477,575 | 10/1984 | Vogel et al. | 422/56 X |
| 4,696,797 | 9/1987 | Keltan | 422/58 X |
| 4,753,776 | 6/1988 | Hillman et al. | 422/101 |
| 4,761,369 | 8/1988 | Steinman | 435/19 |
| 4,783,251 | 11/1988 | Seshimoto et al. | 204/412 |
| 5,096,669 | 3/1992 | Lauks et al. | 422/61 |
| 5,186,843 | 2/1993 | Baumgardner et al. | 210/767 |
| 5,223,219 | 6/1993 | Subramanian et al. | 422/55 |
| 5,262,067 | 11/1993 | Wilk et al. | 422/56 X |

FOREIGN PATENT DOCUMENTS

| | | |
|---|---|---|
| 268025 | 5/1988 | European Pat. Off. . |
| 60-52761 | 3/1985 | Japan . |

OTHER PUBLICATIONS

N. J. Deacan et al. *Experientia* 1976, 32, 384–386.
J. J. Frank et al, *Clin. Chem.* 1978, 24, 1966–1970.
R. G. Haas et al, *Am. J. Clin. Path.* 1982, 77, 216–219.
R. K. Kobos et al. *Clin. Chem.* 1987, 33, 153–158.
D. Yücrl et al. *Clin. Chem*, 1992, 38, 575–577.

*Primary Examiner*—Arlen Soderquist
*Attorney, Agent, or Firm*—Lowe, Price, LeBlanc & Becker

[57] ABSTRACT

The present invention concerns a method of detecting hemolysis in a whole-blood sample, a method of determining an elevation in the potassium ion concentration of a whole-blood sample, an apparatus for detecting hemolysis and/or determining an elevation in the potassium ion concentration in a fluid sample, an apparatus for detecting hemolysis and/or determining an elevation in the potassium ion concentration in a whole-blood sample, and a single-use cartridge containing a plurality of microfabricated biosensors which further contains a hemolysis detection unit.

16 Claims, 7 Drawing Sheets

APPARATUS FOR ESTIMATING THE CHANGE IN AN ANALYTE FROM HEMOLYSIS IN A FLUID SAMPLE

This is a division of U.S. patent application Ser. No. 08/131,527, filed Oct. 4, 1993, which issued as U.S. Pat. No. 5,416,026 on May 16, 1995.

BACKGROUND OF THE INVENTION

1. Field of the Invention

The present invention concerns a method of detecting hemolysis in a whole-blood sample, a method of determining an elevation in the potassium ion concentration of a whole-blood sample, an apparatus for detecting hemolysis in a fluid sample, an apparatus for detecting hemolysis in a whole-blood sample, an apparatus for determining an elevation in the potassium ion concentration of a whole-blood sample, and a single-use cartridge containing a plurality of microfabricated biosensors further containing a hemolysis detection unit.

2. Discussion of the Background

A number of analytes in biological fluids are present in amounts which differ dramatically from their concentration in red blood cells. For example, the potassium concentration inside intact red blood cells is usually about 150 mM and the potassium concentration in a plasma fraction of a normal patient is usually about 4.0 mM.

Procedures for manipulating cells or biological fluid samples containing cells can sometimes result in rupture of the cells, a phenomenon known in the art as "lysis." This phenomenon is particularly common for red blood cells. When intact red blood cells are physically damaged and break open, the phenomenon is known as "hemolysis." For example, hemolysis may occur when a blood sample is drawn from a patient. Hemolysis results in mixing the contents of the red blood cells, which contain relatively high concentrations of potassium and hemoglobin (among other analytes), with the plasma fraction of the blood sample.

Hemolysis is common in blood samples, and may occur when blood contacts foreign surfaces. Hemolysis may be unavoidable, especially during cardiac surgery or cardiac bypass, when there is transfusion or extracorporeal circulation. Hemolysis may also result from improper drawing and handling of biological fluid specimens, and can even occur during centrifugation and separation procedures. Therefore, clinical chemists must know whether hemolysis affects the analyses ordered by clinicians. Many laboratories reject all hemolyzed specimens without considering whether this approach is justified.

In clinical medicine, for example, the potassium concentration in a whole-blood sample is determined by measuring the potassium concentration in the plasma fraction of the whole-blood sample. In view of the fact that the potassium concentration inside red blood cells can be from 25 to 75 times higher than the potassium concentration in blood plasma, hemolysis of only a few red blood cells will result in an artificial elevation of the concentration of potassium in the plasma fraction.

In the medical arts, generally only the potassium concentration in the plasma fraction is important for determining the electrolyte balance of a patient. The potassium concentration in the plasma fraction is used to determine, for example, the sodium/potassium balance, an important indicator of proper nerve conduction, and other fundamental conditions related to acute care known to those in the medical arts. Consequently, hemolysis during sample draw can result in an over-estimate of the true plasma potassium concentration. This can be particularly serious if a patient actually has a low plasma potassium concentration, requiring urgent treatment. In this scenario, a small number of hemolyzed red blood cells can elevate the plasma potassium concentration into the normal range, resulting in no treatment where urgent treatment is required.

In addition to potassium, measurements of the concentration of lactate dehydrogenase and acid phosphatase are significantly affected by hemolysis, and an increase in cholesterol levels may be observed when there is severe hemolysis.

Erythrocytes (red blood cells) contain about 160 times more lactate dehydrogenase, 68 times more acid phosphatase, 40 times more aspartate aminotransferase, and 6.7 times more alanine aminotransferase as does blood plasma (Caraway, Chemical and diagnostic specificity of laboratory tests. Am. J. Clin. Pathol., 1961; 37:445–64). Lactate dehydrogenase and acid phosphatase are the clinically most important enzymes which show significant increases because of hemolysis. Prostatic acid phosphatase (tartrate-inhibited acid phosphatase) is also affected by hemolysis. It is believed that tartrate may not inhibit the increase in enzyme activity resulting from hemolysis (see Yucel et al, Effect on in vitro hemolysis on 25 common biochemical tests. Clinical Chemistry, 1993, 38:575–577).

For this reason, phlebotomists and other medical personnel who are responsible for drawing blood samples are taught techniques that minimize hemolysis. For example, when obtaining a sample by means of a finger or heal-stick, squeezing the site to promote blood flow is known to cause hemolysis, and should be avoided.

The standard clinical chemistry laboratory method for determining if a blood sample has significant hemolysis is to spin the sample in a centrifuge to separate the plasma fraction from the red blood cells, then visually examine the plasma fraction. Hemolysis results in the plasma fraction being contaminated with hemoglobin, which gives an obvious red color to the otherwise yellow plasma. In a typical clinical chemical laboratory, virtually all blood tests performed are based on plasma measurements. Accordingly, centrifuging the blood sample is a satisfactory procedure to determine hemolysis in the clinical laboratory.

As a result, if a test ordered by a physician is known to be subject to interference due to hemolysis (e.g. potassium, lactate dehydrogenase, acid phosphatase; see Yucel et al) and the result is abnormal, the color of the plasma sample will be checked by a laboratory technician. If the plasma fraction shows evidence of hemolysis, a fresh blood sample will generally be obtained.

Although the effects of hemolysis are method-dependent (Frank et al, Effect of in vitro hemolysis on chemical values for serum. Clin. Chem., 1978; 24:1966–1970), even when samples are only slightly hemolyzed, results for lactate dehydrogenase, acid phosphatase, prostatic phosphatase, and potassium analyses must be rejected.

The concentration of free hemoglobin (Hb) in serum can be used as a measure of hemolysis (Yucel et al). For example, serum or blood plasma shows visual evidence of hemolysis when the hemoglobin concentration exceeds 20 mg/dL or is greater than 3.1 µmol/L (Caraway, supra; Sonntag et al, Haemolysis as an interference factor in clinical chemistry. J. Clin. Chem. Clin. Biochem., 1986; 24:127–139). Hemolysis has little effect on constituents that are present at lower concentrations in erythrocytes than in plasma, but a marked effect may be observed for constituents that are present at a higher concentration in erythrocytes than in plasma (Sonntag et al, supra; Frank et al, supra; Brydon et al, The effect of haemolysis on the determination of plasma constituents. Clin. Chem. Acta, 1972; 41:435–438). Hb may also interfere in the colorimetric determination of constituents when certain chromogenic reagents susceptible to oxidation by Hb are used to provide a visual indication of the presence and/or concentration of the constituents.

In addition to the analytes described above (potassium, lactate dehydrogenase, cholesterol, prostatic phosphatase, aspartate aminotransferase, and alanine aminotransferase), concentrations or activities of aldolase, total acid phosphatase, isocitrate hydrogenase, magnesium and phosphate are also increased by hemolysis in biological fluid samples.

For example, when the biological fluid is whole-blood, the inorganic phosphate concentration in the corresponding plasma fraction increases rapidly as the organic esters in the cells are hydrolyzed. Aspartate aminotransferase activity is increased by 2% for each 10 mg hemoglobin per dL of biological fluid sample (Hb/dL). When colorimetric procedures without extraction are used, 10 mg Hb/dL will raise the apparent cholesterol concentration by 5 mg/dL. Ten mg of hemoglobin per dL of biological fluid sample will increase serum lactate dehydrogenase by about 10%, and serum potassium by about 0.6% (see Tietz, "Textbook of Clinical Chemistry," W. G. Saunders and Co. (1986), page 488).

A method and test strip for determining the presence of hemoglobin in urine is known (HEMASTIX™, manufactured by Miles Ames, Elkart, Ind.). However, the HEMASTIX™ test is only semi-quantitative. Further, there is no need to discriminate between red blood cells and Hb in the HEMASTIX™ test, and as a result, red blood cells need not be separated prior to use of HEMASTIX™ strips. In addition, urine usually has an acidic pH, whereas blood serum or plasma has a pH of 7.4. Thus, the method and test strip used to determine the presence of Hb in urine falls short of the need for a method and device for determining hemolysis in whole blood.

Further, methods of separating plasma or serum from whole-blood using a material which separates blood plasma or serum from erythrocytes and leukocytes or from whole-blood are also known (U.S. Pat. Nos. 4,477,575 and 4,816,224). However, these methods and apparatuses have not been used to determine the presence of hemoglobin or an elevation in the concentration of a blood analyte due to hemolysis of red blood cells.

Currently, there is no practical method for determining whether a blood sample is hemolyzed when tested with any analytical system which:

(i) operates on whole-blood, and (ii) is used at the patient's bedside, where a centrifuge is not available.

The present invention seeks to solve this problem by creating a simple method and device for identifying blood samples in which hemolysis has occurred to a level sufficient to result in erroneous measurements of plasma analyte concentrations or activities.

SUMMARY OF THE INVENTION

Accordingly, one object of the present invention is to provide a novel method and apparatus for detecting hemolysis in a biological fluid sample which qualitatively determines whether a sufficient number or concentration of intact red blood cells have been hemolyzed to elevate subsequent analyte measurements using the biological fluid sample.

A further object of the present invention is to provide a novel method and apparatus for detecting hemolysis in a whole-blood sample which qualitatively determines whether a sufficient number or concentration of intact red blood cells have been hemolyzed to elevate subsequent analyte measurements using the biological fluid sample.

A further object of the present invention is to provide a novel method and apparatus for estimating the level of hemolysis, or the number of hemolyzed red blood cells per unit volume, in a biological fluid sample.

A further object of the present invention is to provide a novel method and apparatus for estimating the level of hemolysis or the number of hemolyzed red blood cells per unit volume in a whole-blood sample.

A further object of the present invention is to provide a novel method and apparatus for estimating the elevation in potassium ion concentration in a biological fluid sample due to hemolysis.

A further object of the present invention is to provide a novel method and apparatus for estimating the elevation in potassium ion concentration in a whole-blood sample due to hemolysis.

A further object of the present invention is to provide an improved single-use cartridge comprising a plurality of microfabricated biosensors, which qualitatively and/or quantitatively determines an elevation in the concentration of an analyte due to hemolysis, where the analyte has a relatively higher concentration in intact red blood cells and a relatively lower concentration in the plasma fraction.

These and other objects, which will become apparent during the following detailed description of the preferred embodiments, have been provided by a novel method and apparatus for detecting hemolysis in a biological fluid sample, in which the method comprises:

(a) contacting a whole-blood sample comprising intact red blood cells with a dry separation material, said material having physical characteristics effective to separate a fraction, which contains extracellular hemoglobin that may be present in said sample, from the intact red blood cells;

(b) allowing said sample to remain in contact with said material for a period of time sufficient to effect said separation; and (c) detecting the presence of extracellular hemoglobin in said fraction, and in which the apparatus comprises:

(a) a dry separation material to which a fluid sample may be applied, said material having physical characteristics effective to separate a fraction of said sample, which fraction would contain a representative concentration of any extracellular hemoglobin that may be present in said sample; and (b) a detection means for ascertaining the concentration of said extracellular hemoglobin in said fraction.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
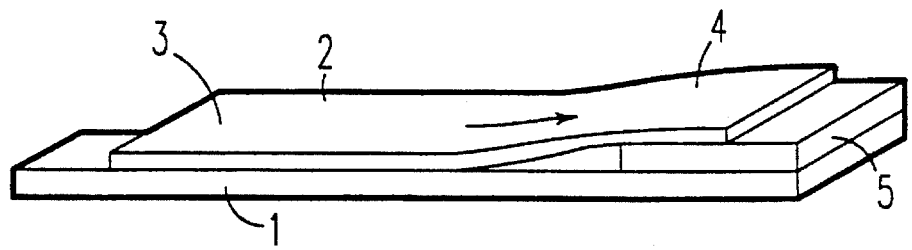
FIG. 1 shows an embodiment of the present apparatus.

In the present application, the term "whole-blood" refers to freshly drawn blood which is tested before it clots; or to a conventionally-drawn blood sample, which may be drawn into a vacutainer, and which may contain an anticoagulant, such as lithium-heparin, etc., or to which one or more other standard clinical agents may be added in the course of routine clinical testing.

The term "about" generally refers to a reasonably expected fluctuation in experimentally-determined values of various analytes well-known to those in the field of clinical chemistry. Such reasonably expected fluctuations may differ, depending on the accuracy and the sensitivity of the techniques used.

In the present invention, either "serum" or "plasma" refers to the fraction of whole blood separated from red blood cells. "Serum" generally refers to the fraction of whole blood to which one or more anticoagulants, such as lithium-heparin, have been added (anticoagulated whole blood), and in which red blood cells have been removed. Serum is typically used in the medical and clinical arts for measurement of analytes. "Plasma" generally refers to the fraction of whole blood which has not been anticoagulated, but which has had red blood cells removed. Plasma is typically used in the medical and clinical arts to replace blood in patients, usually intravenously or by injection.

In the present application, the term "elevation" refers to the increase in concentration of an analyte above the concentration that would otherwise have been present in the fraction, had the fluid sample been free from hemolysis.

I. A Method Of Detecting Hemolysis In A Whole-Blood Sample

There exists a need in the medical and clinical arts for a method which quickly determines whether a biological fluid sample contains hemolyzed red blood cells, and which does not require use of a centrifuge. The need is particularly strongly felt in methods which determine the presence or concentration of analytes in whole-blood samples. Accordingly, the present invention encompasses a method of detecting hemolysis in a whole-blood sample, comprising the steps of:

(a) contacting a whole-blood sample comprising intact red blood cells with a dry separation material, the material having physical characteristics effective to separate a fraction, which contains extracellular hemoglobin that may be present in the sample, from the intact red blood cells;

(b) allowing the sample to remain in contact with the material for a period of time sufficient to effect the separation; and (c) detecting the presence of extracellular hemoglobin in the fraction.

In the present method, the fraction separated from intact red blood cells includes plasma and serum. The sample may be diluted, treated with a solution or reagent, or have an internal standard added thereto, as long as such treatment does not chemically modify the analytes or affect the separation behavior of the separated fraction. For example, physiological saline may be added to dilute the sample. However, deionized water should not be added to the sample, since addition of deionized water to whole-blood may result in hemolysis.

The detection step in the method may comprise visually inspecting the fraction for the presence of a color hue. In this embodiment of the present method, the color hue corresponds to an estimated concentration of extracellular hemoglobin of about 20 mg/dL, which is equivalent to lysis of about 100 red blood cells per µL of whole-blood. As described above, blood plasma shows visual evidence of hemolysis when the hemoglobin concentration exceeds 20 mg/dL (Tietz, page 488), resulting in a color change from a yellow hue to a red or pink hue.

II. A Method Of Estimating The Concentration Of Hemoglobin In A Whole-Blood Sample By Comparing The Color Of The Separated Fraction With An External Color Hue The present invention also encompasses a method of estimating the concentration of Hb in a whole-blood sample, and correspondingly, the number of hemolyzed red blood cells per unit volume or concentration of hemolyzed red blood cells in a whole-blood sample, by comparing the color hue of the separated fraction with a number of different color hues on a chart. The chart displays a number of characteristic color hues corresponding to the colors associated with a range of predetermined Hb concentrations in plasma. Thus, the present method may further comprise comparing the color hue of the separated fraction to a colored chart displaying a variety of color hues, each of the color hues being indicative of an estimated concentration of extracellular hemoglobin present in a given separated fraction.

Alternatively, the present detection step may comprise contacting the separated fraction with a chromogenic reagent. Any extracellular hemoglobin that may be present in the separated fraction reacts with the chromogenic reagent to provide a color change. Preferably, the color change is visually detectable.

Detection of hemoglobin in this embodiment depends on the peroxidase activity of heme proteins, which catalyze the reduction of a peroxide. This reaction requires an organic peroxide and a hydrogen donor (reduced chromogen). Such molecules include o-toluidine, guaiac, diisopropylbenzene dihydroperoxide and tetramethylbenzidine. After reacting with Hb, the oxidized chromogens produce the desired color change.

The chromogenic agent may be quenched with a quenching agent after a certain period of time, dependent upon the rate at which the separated fraction traverses the separation material and contacts both the chromogenic reagent and the quenching agent, and the rate at which the quenching agent and chromogenic reagent diffuse through the separated fraction to react with each other. This embodiment provides end-point measurements ("stops"), so the concentration of Hb is related to the intensity of the final color developed after a certain length of time. In a time-based or rate-based "stop" method, after a predetermined period of time, the intensity of the final color may be measured, or alternatively, an electrochemical measurement may be taken, to determine the concentration of Hb.

A reagent system which is used to determine the presence of cholesterol in serum is a cholesterol esterase-cholesterol oxidase-peroxidase system (for example, as described in U.S. Pat. Nos. 4,477,575 and 4,816,224). The peroxidase activity of Hb interferes with such a test. Accordingly, the present method can be used in conjunction with the method of colorimetrically analyzing serum cholesterol described in U.S. Pat. Nos. 4,477,575 and 4,816,224 to determine the elevation in peroxidase activity due to Hb.

o-Toluidine is used in very small quantities in a commercially available dipstick (HEMASTIX™, Miles Ames Company, Elkhart, Ind.), which is used for determining the presence of hemoglobin or myoglobin in urine. The amount of o-toluidine used in this embodiment of the present method is preferably very small.

o-Toluidine is sensitive to about 2 mg of Hb/dL of urine, equivalent to about 10 erythrocytes/µL of urine or 10 erythrocytes/µL of whole-blood, respectively. Thus, o-toluidine toluidine is very sensitive to Hb (Tietz, page 1562). A negative test (the absence of any blue or greenish color) means that no significant hemolysis has occurred in the specimen examined. A positive test (the presence of a blue or greenish color) means that significant hemolysis has occurred in the specimen examined. More specifically, a negative test means that the estimated concentration of extracellular hemoglobin is less than 2 mg/dL of the separated fraction, while a positive test means that the estimated concentration of extracellular hemoglobin is at least 2 mg/dL, or alternatively, that about 10 erythrocytes/1 µL of whole-blood have been hemolyzed.

To optimize the sensitivity of the test, the chromogenic reagent is impregnated into the detection area of the strip in gradually increasing amounts, until sufficient chromogenic reagent is present to react with any amount of hemoglobin which may be present in the separated fraction. In optimizing the test, several strips, each containing a different amount of chromogenic reagent, are individually tested. A concentration of chromogenic reagent may then be selected which provides the desired color development in a desired length of time. The color development is thus independent of the dry separation material, but dependent on the level of hemolysis.

False positive results may be observed, however, if the sample container has been contaminated with hypochlorite solution, or if peroxidase-containing bacteria are present in the sample. Positive results may also occur if free myoglobin or intact erythrocytes are present in the sample. As will be discussed below, it is therefore essential that the dry separation material separate intact red blood cells from the fraction which may contain Hb. However, free myoglobin is found typically only in samples obtained from heart attack patients. Accordingly, a blood sample drawn from a known or suspected heart attack patient may be treated with anti-myoglobin antibodies prior to hemolysis detection.

The detection step of the present method may alternatively be performed with the aid of a reflectance meter, the meter providing a reading that is a function of the concentration of extracellular hemoglobin present in the fraction. Thus, the present method may further comprise the steps of irradiating the separated fraction with light, and determining the reflectance of the light due to hemoglobin in the separated fraction.

When measuring the reflectance due to hemoglobin in the separated fraction directly (where no chromogenic reagent is present), the light may be a wavelength for which hemoglobin exhibits a maximum absorbance. Typically, however, broad-band visible light is used to measure the reflectance. The reflectance is calibrated against a white surface (for example, the unused dry separation material). Reflectance of the dry separation material containing a separated serum or plasma fraction is then based on a scale of grayness (for example, the less white color, the lower the reflectance). Further measurements performed on samples having a known concentration of Hb provide data points on which quantitative reflective measurements can be based. A graph of reflectance versus Hb concentration is plotted. The graph can then be used to determine the Hb concentration of the separated fraction of a whole-blood sample based on the reflectance of the separated fraction.

III. Method Of Estimating The Elevation Of An Analyte In A Whole-Blood sample Due To Hemolysis The present method may further comprise, after the detecting step, the step of estimating the elevation of an analyte in the sample which is due to the hemolysis of red blood cells. In a preferred embodiment, the present method estimates the elevation of an analyte selected from the group consisting of potassium ion, lactate dehydrogenase, and acid phosphatase. The present method is particularly suitable for estimating the elevation of potassium ion due to the hemolysis of red blood cells.

In the embodiment of the present method which further comprises the step of estimating the elevation of an analyte in the sample, the method may further comprise the step of adjusting the apparent concentration of the analyte to account for the proportion of same which is due to the hemolysis of red blood cells, after the estimating step.

Microfabricated biosensors for use in detecting and determining the presence and/or concentration of a variety of analytes, including potassium, are disclosed in U.S. Pat. No. 5,200,051, incorporated herein by reference.

In the embodiment of the present method of determining the elevation in the potassium ion concentration due to hemolysis of intact red blood cells in a whole-blood sample, the method comprises:

(a) contacting a whole-blood sample comprising intact red blood cells with a dry separation material having physical characteristics effective to separate a plasma fraction, which contains extracellular hemoglobin that may be present in the sample, from the intact red blood cells;

(b) allowing the sample to remain in contact with the material for a period of time sufficient to effect the separation;

(c) estimating the quantity of extracellular hemoglobin in the plasma fraction; and (d) estimating the elevation of the potassium ion concentration in the sample which is due to hemolysis.

Preferably, the method of determining the elevation in the potassium ion concentration due to hemolysis of intact red blood cells specifically detects a level of hemolysis sufficient to cause an elevation of the potassium concentration by at least 0.1 mM above the potassium concentration which would otherwise have been present in the plasma fraction had the whole-blood sample been free from hemolysis. An elevation of the potassium concentration by 0.1 mM corresponds to hemolysis of a relatively small percentage of red blood cells per μL of whole-blood, assuming a normal hematocrit level (about 40%).

Alternatively, the method of determining the elevation in the potassium ion concentration due to hemolysis of intact red blood cells is performed in a single-use whole-blood analysis cartridge, which comprises the dry separation material and an ion-selective electrode for measuring the concentration of potassium ion. Preferably, the potassium ion-selective electrode is microfabricated on a silicon chip.

The present method of determining the elevation in the potassium ion concentration due to hemolysis of intact red blood cells may further comprise the step of comparing the elevation of the potassium ion concentration to a pre-selected value of hemolysis, and rejecting as unreliable for clinical purposes an elevation above the pre-selected value. This may be accomplished by comparing the color of the separated fraction, which may also be contacted with the chromogenic reagent described above, with a color hue corresponding to the color of a standard plasma sample containing the concentration of Hb which results from the pre-selected value of hemolysis.

For example, 10 mg of hemoglobin per 1 μL of serum results in a 0.6% elevation in the serum potassium ion concentration (Tietz, p. 488). The relationships between hemolyzed red blood cells, the concentration of Hb, and the elevation of blood analytes such as potassium ion concentration are linearly dependent upon each other. As a result, those of ordinary skill in the art will be able to pre-select a value of hemolysis which corresponds to both a known concentration of Hb in plasma and the corresponding color thereof, which in turn correlates to a pre-selected elevation in the potassium ion concentration to be rejected as unreliable for clinical purposes.

IV. An Apparatus For Detecting Hemolysis In A Fluid Sample, Particularly A Whole-Blood Sample A further aspect of the present invention encompasses an apparatus for detecting hemolysis in a fluid sample, comprising:

(a) a dry separation material to which a fluid sample may be applied, the material having physical characteristics effective to separate a fraction of the sample, which fraction would contain a representative concentration of extracellular hemoglobin that may be present in the sample; and (b) a detection means for ascertaining the concentration of the extracellular hemoglobin in the fraction.

The present apparatus is particularly useful for detecting hemolysis in biological fluid samples which contain erythrocytes, such as whole-blood, or which may contain erythrocytes, such as urine. The present apparatus is most suitable for whole-blood samples. Therefore, the present invention also encompasses an apparatus for detecting hemolysis in a whole-blood sample, comprising:

(a) a dry separation material to which a whole-blood sample having intact red blood cells may be applied, the material having physical characteristics effective to separate a fraction, which contains extracellular hemoglobin that may be present in the sample, from the intact red blood cells; and (b) a detection means for ascertaining the presence of extracellular hemoglobin in the fraction.

The present dry separation material is a dry material which separates biological fluids from intact red blood cells rapidly by wicking action, and does not cause visible hemolysis. The phrase "wicking action" refers to the ability of the present dry separation material to transport fluid from the site where it is introduced to the dry separation material to the remainder of the dry separation material in a radial fashion. By contrast, red blood cells are not transported readily along the material, and are thus retarded by the dry separation material, relative to the separated fraction. "Wicking action" is also known in the art as "capillary forces," which are described in U.S Pat. Nos. 4,816,224 and 4,477,515 from column 5, line 64 through column 6, line 5, and "capillary action," which is mentioned in U.S. Pat. No. 5,096,669 (columns 48–51). Preferably, the present dry separation material contains no chemically interfering substances, and does not significantly bind non-cellular components of biological fluid samples.

Preferably, the present dry separation material is a blend of several different types of fibers formed into a single-layer composite fibrous sheet using conventional paper-making technology, described in U.S. Pat. No. 5,186,843, incorporated herein by reference. Alternatively, the present dry separation material also includes a composition comprising a layer of glass fibers, which may optionally further contain an organic polymer binder, described in U.S. Pat. Nos. 4,816,224 and 4,477,575, incorporated herein by reference. A particularly preferred dry separation material is commercially available from Ahlstrom Filtration, sold under the trademark CYTOSEP™.

The composite fibrous sheet suitable for use in the present apparatus as a dry separation material comprises a blend of glass microfibers, cellulose fibers, and synthetic sample fibers, intermixed in a randomly dispersed fibrous matrix. Synthetic binder fibers may be added to provide increased tensile strength. This composite fibrous sheet does not cause hemolysis, an essential requirement of the present dry separation material.

The present dry separation material may be in the form of a strip, in which the dimensions include a length of from 5 to 50 mm, a width of from 1 to 10 mm, and a thickness of from 0.1 to 3.0 mm. Preferably, the physical characteristics of the dry separation material include dimensions of from 10 to 40 mm length, from 3 to 7.5 mm in width, and from 0.2 to 1.0 mm in thickness. A length about two centimeters and a thickness of about 0.3 mm of the dry separation material gives adequate separation in about one minute.

As shown in FIG. 1, the present apparatus may further comprise a stiff substrate 1 supporting the dry separation material 2. Preferably, however, the dry separation material is sufficiently strong or stiff as to not require a supporting substrate. Accordingly, the present apparatus may consist of the dry separation material and the detection means.

The dry separation material may separate red blood cells from the fluid fraction to be separated along any dimension of the material (i.e., lengthwise, widthwise or thicknesswise). As shown in FIG. 1, when separating the fraction lengthwise (in the direction of the arrow), the whole-blood sample is applied at a site toward one end 3 of the dry separation material. The fraction to be separated is transported radially by the wicking action of the dry separation material away from the application site. When the separated fraction reaches a site near or at the end 4 opposite the end containing the application site, the detection means is then used to determine the presence of hemoglobin or to estimate the level of hemolysis.

The phrases "near the end" and "toward one end" refer to a location between the midpoint and the endpoint of the axis of the relevant dimension of separation (length, width or both). Preferably, the location is between the endpoint of the axis (the outermost edge of the dry separation material) and a point one-third of the distance along the dimensional axis, inclusive of the endpoint and the point one-third of the distance along the dimensional axis.

Figure 3:
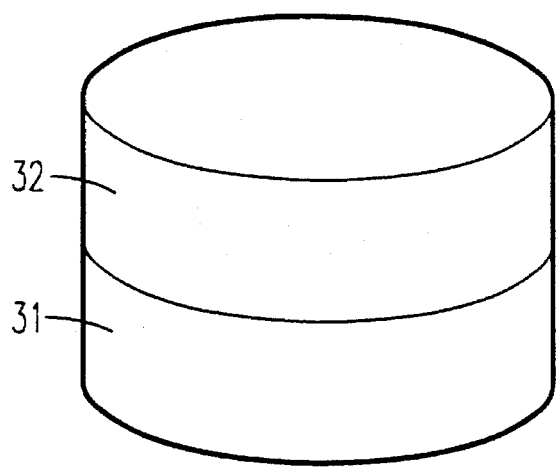
FIG. 3 shows a third embodiment of the present apparatus, suitable for use in an embodiment of the present single-use cartridge.

Alternatively, as shown in FIG. 3, the present dry separation material may separate the fraction from intact red blood cells along the axis of thickness of the material. In this embodiment, the whole-blood sample is applied to the available surface of the dry separation material 31, where the fraction to be separated is transported by wicking action along the thickness axis of the dry separation material to the layer of material 32 attached to the opposite surface. In this embodiment, the apparatus may further comprise one or more layers of material 32 which:

(1) do not hemolyze red blood cells, (2) do not bind chemical or non-cellular components of blood plasma or serum, and (3) effectively prevent the whole-blood sample from being seen or detected.

Suitable materials for accomplishing these objectives are described in U.S. Pat. Nos. 5,186,843, 4,816,224 and 4,477,575.

Similar to the method for detecting hemolysis in a whole-blood sample, the detection means of the present apparatus may comprise a colored chart displaying at least one color hue of an estimated concentration of extracellular hemoglobin present in a given separated fraction.

Optionally, the present detection means may comprise a chromogenic reagent that reacts with the extracellular hemoglobin to provide a color change. As shown in FIG. 1, the present apparatus may therefore further comprise a reagent pad 5, impregnated with the chromogenic reagent, located near or at one end of the dry separation material. Alternatively, as shown in FIG. 3, a reagent pad 32 may be layered onto a surface of the dry separation material.

Alternatively, the chromogenic reagent may be applied directly to the dry separation material. In such a case, the chromogenic reagent may be dissolved in an appropriate solvent, applied to the dry separation material by, for example, spraying or dipping, then the separation material is dried. Techniques for applying the chromogenic reagent to the dry separation material are conventional, and known to those of ordinary skill in the art. The solvent may include organic solvents, such as acetone, methylene chloride, methanol, ethanol, or the like, if the chromogenic reagent is not water-soluble. If the chromogenic reagent is water-soluble, the solvent may be distilled, deionized water or an appropriate buffer, such as a standard phosphate buffer. Of course, where appropriate, mixtures of water and water-soluble or water-miscible organic solvents are also acceptable.

When the dry separation material is used to separate the fraction from intact red blood cells lengthwise or widthwise, the chromogenic reagent may be applied to the end of the dry separation material opposite that to which the whole-blood sample is applied. Alternatively, when the dry separation material separates the fraction from intact red blood cells along its thickness, the chromogenic reagent may be applied to the surface of the dry separation material opposite that to which the whole-blood sample is applied.

Accordingly, the present apparatus may consist of the dry separation material, a chromogenic reagent located towards one end or on one surface of the dry separation material, and the detection means.

Figure 2:
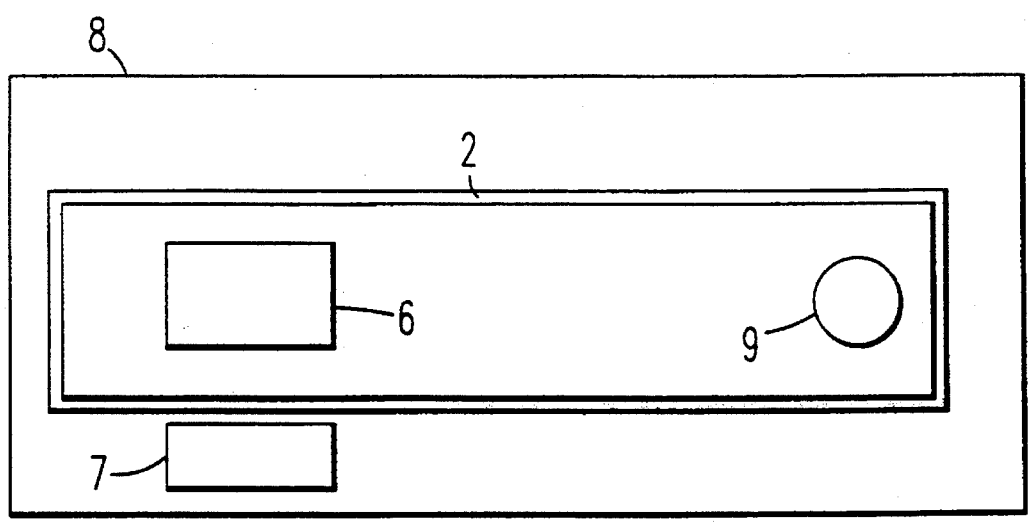
FIG. 2 shows a second embodiment of the present apparatus.

Optionally, as shown in FIG. 2, the present apparatus may be provided with a viewing region 6, next to which the detection means (a colored chart) 7 is located. The viewing window may be designed to substantially exclude from view that portion of the separated sample which contains the intact red blood cells (see FIG. 2). Preferably, the viewing region is located a sufficient distance along the separation material and away from the site where the sample is applied so that red blood cells do not reach the viewing region.

Figure 4A:
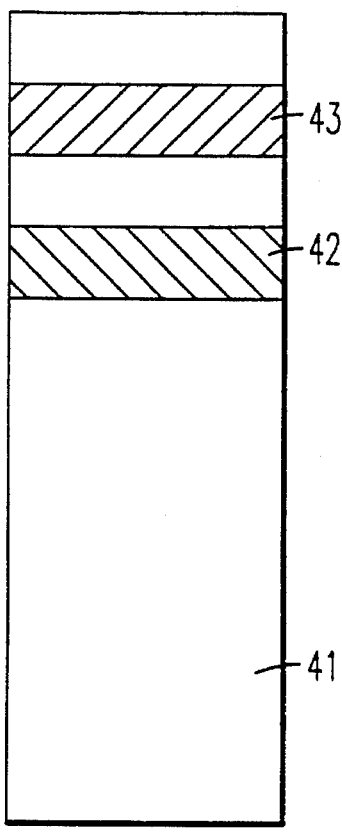
FIG. 4A and 4B show embodiments of the present hemolysis detection device, incorporating both a chromogenic reagent and a "stop" or quenching reagent.
Figure 4B:
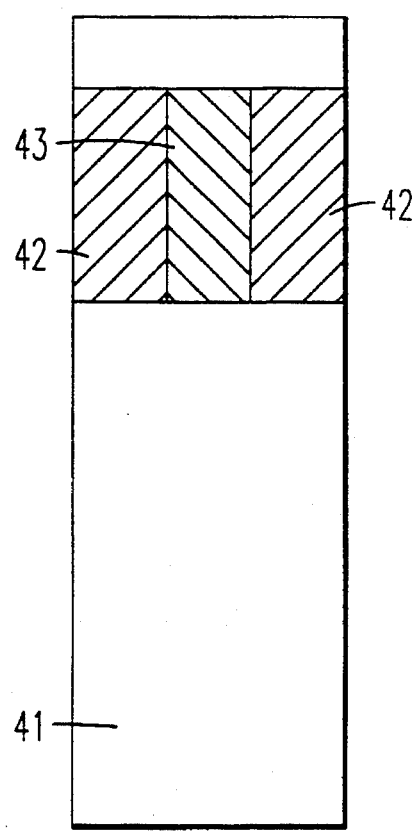

Alternatively, as shown in FIGS. 4A and 4B, a chromogenic reagent may be used in conjunction with a quenching agent, which "stops" the reaction between Hb and the chromogenic reagent. The quenching agent may be located on the dry separation material or in a pad attached thereto, for example, at a location 43 further from the location at which the whole-blood sample is applied 41 than the location containing the chromogenic reagent 42 (FIG. 4A). Alternatively, the location of the quenching agent 43 may be the same distance along the dry separation material as the location of the chromogenic reagent 42 (FIG. 4B).

V. A Single-Use Hemolysis Detection Cartridge

Figure 5:
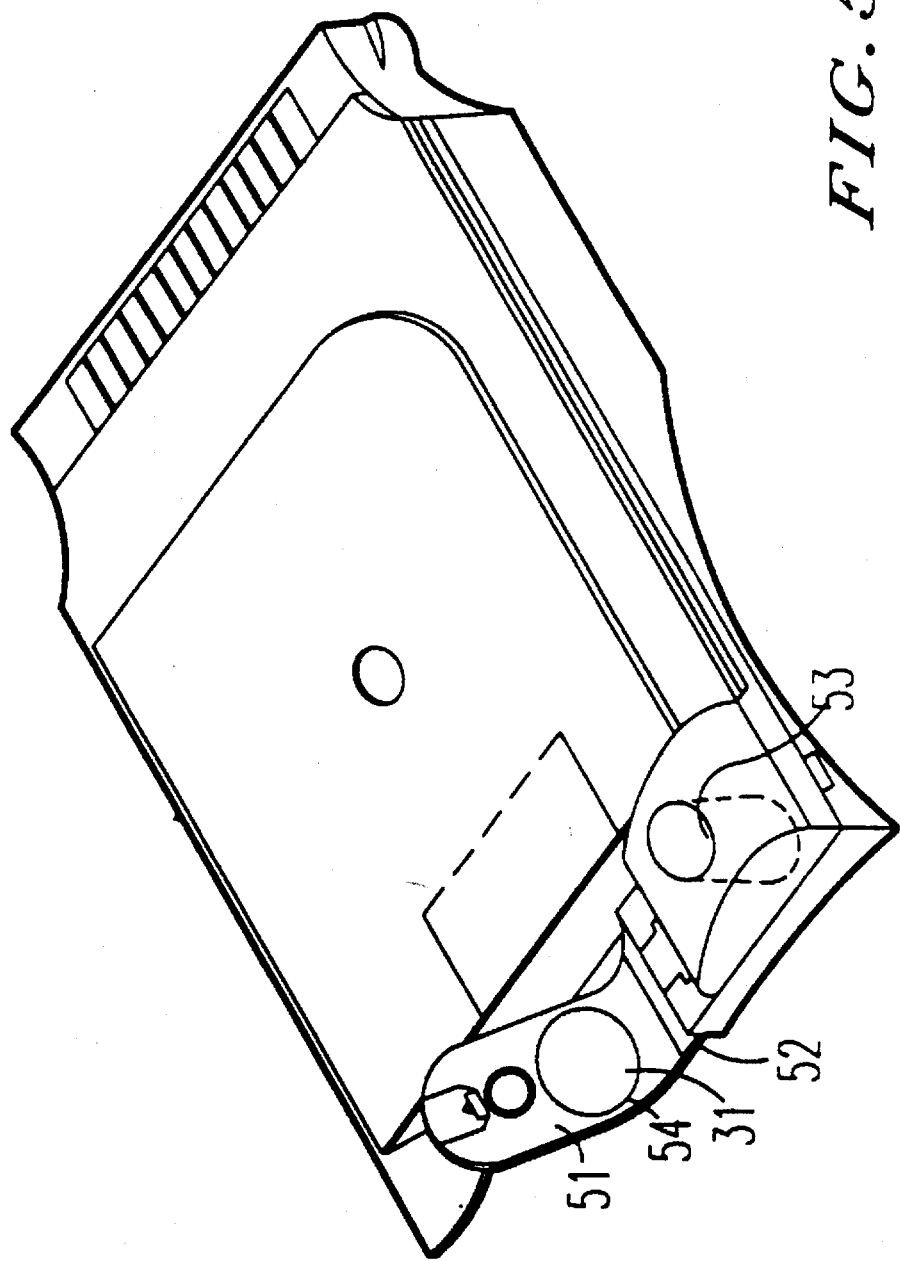
FIG. 5 is a top view of an embodiment of the present single-use cartridge employing the hemolysis detection device of FIG. 3.
Figure 6A:
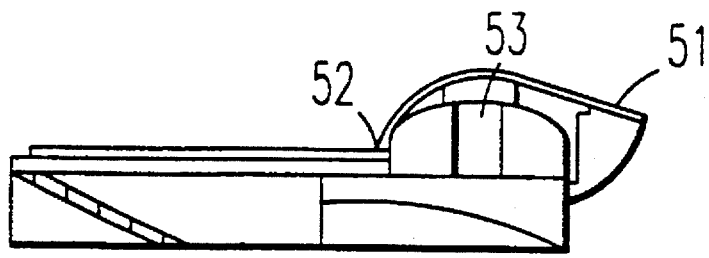
FIG. 6A is a side view of the single-use cartridge of FIG. 5.

The present apparatus is particularly suited for use as a single-use cartridge, and accordingly, may further comprise or further consist of a container 8 surrounding the dry separation material and an orifice 9 for introduction of the sample, as shown in FIG. 2. The single-use cartridge may also further comprise or further consist of means for sealing the orifice. For example, as shown in FIG. 5, a sealable cap 51 on a flexible hinge 52 may be used to seal the orifice after introduction of the whole blood sample therethrough. FIG. 6A shows the cap 51, hinge 52 and cartridge orifice 53 in a closed position.

The single-use cartridge is disposable and self-contained, and uses a very small amount of blood. For example, from 10 to 100 microliters, or more preferably, about 60 microliters ($\mu$L) of whole blood are used in the present single-use cartridge. Therefore, the present single-use cartridge presents minimal risks of exposure to contaminated whole blood samples, both to individuals handling the cartridge and to the environment.

VI. A Hemolysis Detection Device Further Comprising A Colored Chart

In a preferred embodiment, the present apparatus exemplified in FIG. 2 further comprises a colored chart 7 positioned within view of the window, the colored chart displaying at least one color hue indicative of an estimated concentration of extracellular hemoglobin present in a given plasma fraction. The color hue correlates to a predetermined elevation in the potassium concentration in the plasma fraction, preferably an elevation of at least 0.5 millimole per liter, and particularly preferably at least 0.1 millimole per liter.

In a further preferred embodiment of the apparatus of FIG. 2, the colored chart comprises at least two color hues, each of which is indicative of an estimated concentration of extra cellular hemoglobin present in a given plasma fraction, similar to the description above for the present method of estimating the concentration of Hb in a whole-blood sample. For example, a yellow hue, correlating to a concentration of less than 20 mg/dL of Hb, may indicate an acceptable sample, whereas a pink hue, correlating to a concentration of greater than 20 mg/dL of Hb, may indicate an unreliable sample. For semi-quantitative estimations, however, the colored chart may contain from three to twelve color hues.

In a further embodiment of the present invention, the detection means of the present apparatus may comprise a reflectance meter including a light source and a light detector, the light source being positioned to permit an incident light beam from the light source to strike the separated fraction to provide a reflected light beam and the light detector being positioned to permit detection of the reflected light beam.

VII. A Single-Use Cartridge For Detecting Hemolysis and Measuring Analytes In Blood or Other Fluids The present single-use hemolysis detection device may be either independent from or incorporated into a disposable device and hand-held reader, capable of performing a variety of electrochemical measurements on blood or other fluids. An extremely useful bedside analytical system for conducting a variety of electrochemical measurements on blood or other fluids is the i-STAT system (manufactured by I-Stat Corp., Princeton, N.J.), based on a system of microfabricated biosensors, and described in U.S. Pat. No. 5,096,669 and U.S. Design Patent No. 337,164, each of which is incorporated herein by reference. Accordingly, the present apparatus can be adapted for use in a system of microfabricated biosensors, such as the i-STAT system.

As shown in FIG. 5, a small portion of the blood introduced into the i-STAT device enters the cartridge orifice 53. The cap 51 is placed over cartridge orifice 53 such that dry separation material 31 comes into contact with the whole-blood sample in the orifice. The plasma or serum fraction separates from whole blood cells by wicking action, traversing the dry separation material 31 and contacting a layer of detection material 32, which may be impregnated with a chromogenic reagent.

Figure 6B:
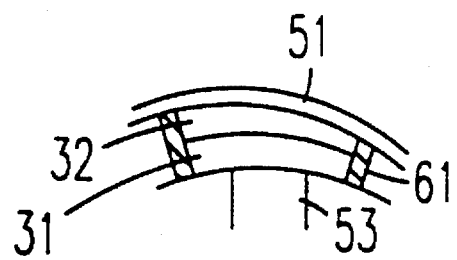
FIG. 6B is an enlarged side view of the hemolysis detection device of FIG. 3 employed therein.

An end-on view of this device is depicted in FIG. 6A, described above. FIG. 6B is a detailed side-on view of a portion of the cap 51, cartridge orifice 53 and hemolysis detection device (dry separation material 31 and visualization material layer 32) in this embodiment of the invention. A rubber or plastic O-ring 61 surrounds dry separation material 31 and visualization material layer 32, to create an air tight seal, required for proper functioning of the i-STAT cartridge comprising a plurality of microfabricated biosensors.

Accordingly, the present invention further encompasses a single-use cartridge, comprising a plurality of microfabricated biosensors arranged to determine the presence or concentration of one or more physiological analytes in a whole-blood sample, the assembly further comprising a hemolysis detection unit comprising:

(a) a dry separation material to which a portion of the whole-blood sample may be applied, the material having physical characteristics effective to separate a fraction of the sample, which fraction would contain a representative concentration of extracellular hemoglobin that may be present in the sample; and (b) a detection means for ascertaining the concentration of the extracellular hemoglobin in the fraction.

Preferably, the microfabricated biosensors include a microfabricated potassium ion selective electrode and reference electrode, used to determine the concentration of potassium ion in the sample. Furthermore, in this embodiment, human visualization may be replaced by the use of a reflectance meter to more accurately quantify the hemoglobin concentration, and therefore, the elevation in the plasma analyte concentration. In this embodiment, for example, an accurate quantitative measurement of hemoglobin enables correction of the potassium measurement performed by the i-STAT potassium ion-selective electrode.

The resolution of the i-STAT potassium ion-selective electrode is sufficient to reliably report potassium concentrations to ±0.1 mM. Accordingly, the present single-use cartridge is preferably designed to detect hemolysis sufficient to cause an elevation of the potassium concentration in the plasma fraction of the whole-blood sample by at least 0.1 mM.

Figure 7:
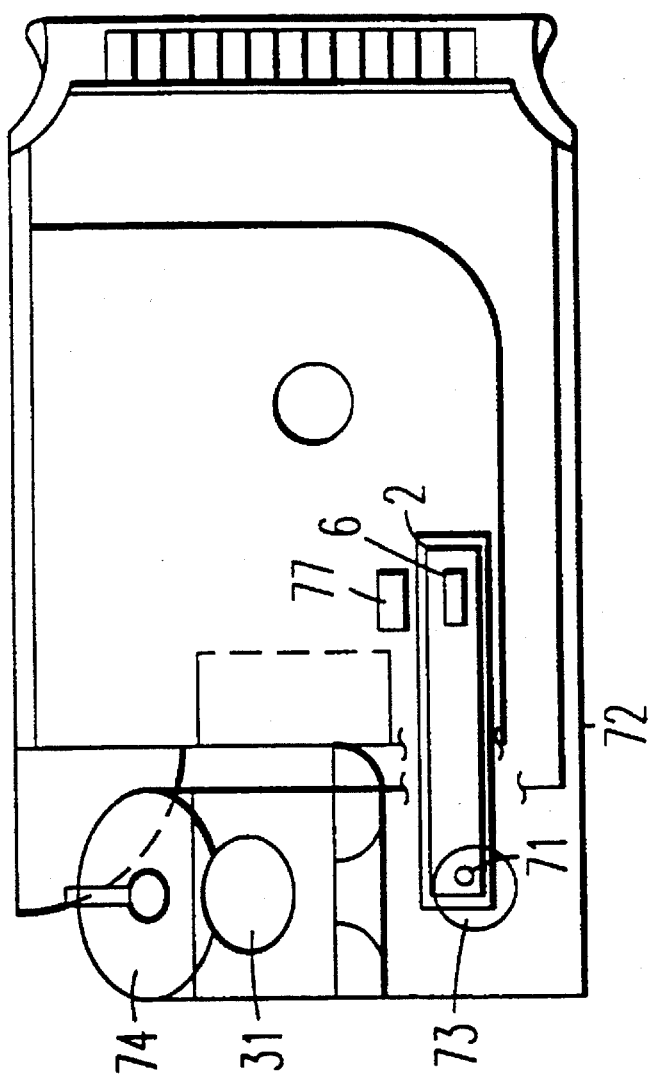
FIG. 7 is a top view of a single-use cartridge according to the present invention incorporating a modified hemolysis detection device according to FIG. 2.

In a further embodiment, the present apparatus can be incorporated directly into the cartridge housing 72 of the i-STAT single-use cartridge as shown in FIG. 7, or close by, for easy qualitative reading by the user. In the device shown in FIG. 7, the hemolysis detection device of FIG. 2 is slightly modified for use therein. The modification essentially involves exchanging the container 8 shown in FIG. 2 for the single-use cartridge housing 72 of FIG. 7.

In this embodiment, the whole-blood sample is introduced into cartridge orifice 73, located directly above hemolysis detection device sample orifice 71. After closing cap 74, the whole-blood sample is forced through hemolysis detection device sample orifice 71, where it contacts one end of dry separation material 2. The plasma or serum fraction separates from whole blood cells by wicking along dry separation material 2, where eventually it contacts visualization region 6. A window in the cartridge housing either directly above visualization region 6 (see FIG. 7) or below visualization region 6 (see FIG. 8) enables detection. Colored chart 77 (FIG. 7) or 87 (FIG. 8) may be provided, in accordance with embodiments of the present invention involving a color chart, as described above.

Figure 8:
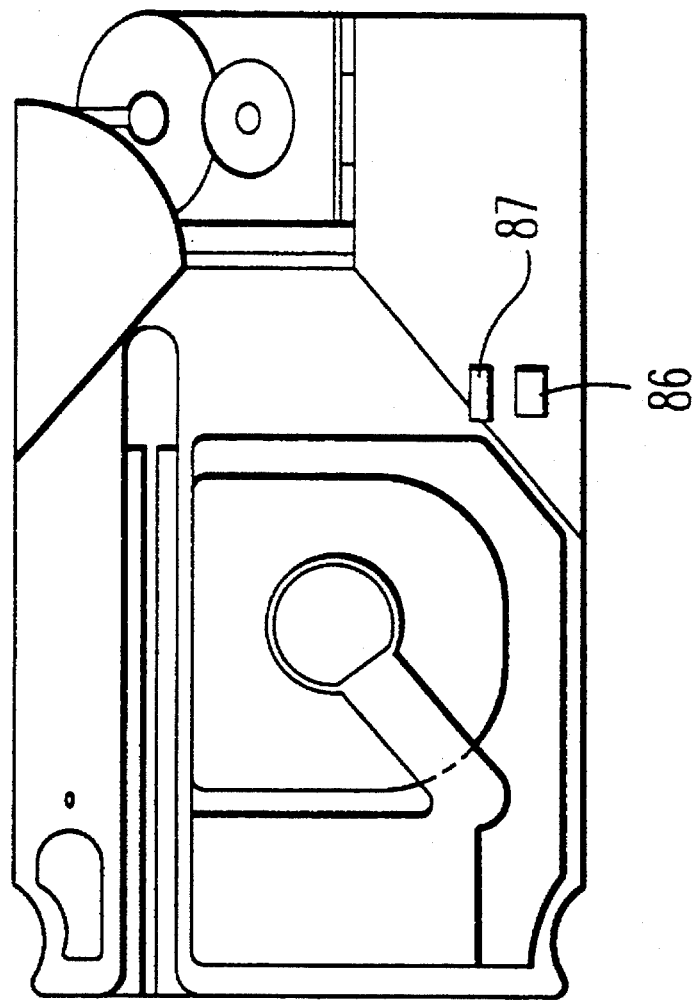
FIG. 8 is a bottom view of the single-use cartridge of FIG. 7.
Figure 9A:
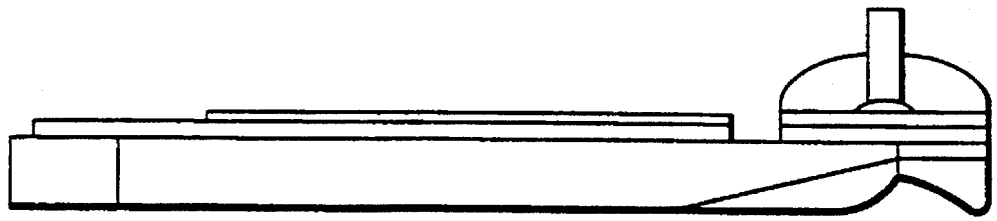
FIG. 9A shows a side view of the embodiment of the single-use cartridge shown in FIG. 7.
Figure 9B:
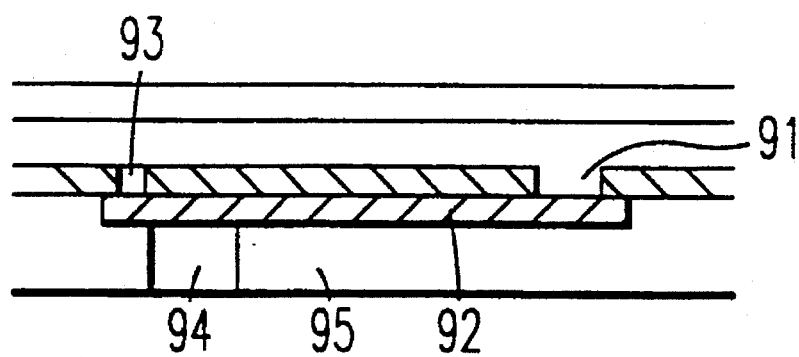
FIG. 9B shows enlarged details of the hemolysis detection device therein.

FIG. 9 shows a side-on view of the single-use cartridge of FIGS. 7 and 8. In the device of FIG. 9, a hemolysis detection device sample orifice 91 for contacting the whole blood sample with dry separation material 92 is located just beyond the blood port gasket. The plasma or serum fraction wicks along dry separation material 92, thus becoming separated from whole blood cells. In this embodiment, a vent 93 is necessary to allow air to escape from the dry separation material as the plasma or serum fraction traverses it. For convenience, visualization window 94 is located in the underside of cartridge housing 95, thus corresponding with the embodiment shown in FIG. 8.

As described in U.S. Pat. No. 5,096,669, the single-use cartridge comprising a plurality of microfabricated biosensors is inserted into a reading machine to measure the concentration of analytes in the blood sample. Accordingly, visualization of the separated fraction using the hemolysis detection device may be performed either before or after inserting the single-use cartridge into the reading device.

Other features of the invention will become apparent in the course of the following descriptions of exemplary embodiments which are given for illustration of the invention and are not intended to be limiting thereof.

EXAMPLE 1

Lithium-heparinized blood was frozen for one hour and then thawed to hemolyze the red blood cells. Aliquots of lithium-heparin blood were then added to a number of samples of unhemolyzed whole-blood in amounts sufficient to provide a range of Hb concentrations in the serum fractions. The samples were then thoroughly mixed. Samples were prepared in this manner having normal potassium values (about 4 mM) and having potassium concentrations elevated from 0.1 to 10 mM due to hemolysis. The potassium concentration in the spun serum fraction of each sample was then determined on a Beckman Astra Autoanalyzer (Beckman Instruments). The potassium concentration of each whole blood sample was also determined with i-STAT 6+ cartridges and the Portable Clinical Analyzer (i-STAT, Princeton, N.J.). In this manner, it was possible to prepare a sample which has visible signs of hemolysis on inspection of the serum after spinning (i.e., centrifuging), and yet has the same measured potassium concentration as one with no visible signs of hemolysis (i.e. where the potassium elevation is less than 0.1 mM). This is because a change in potassium concentration of less than 0.1 mm represents the resolution of both the Beckman-Astra Autoanalyzer and the i-STAT system.

EXAMPLE 2

A simple device, used to detect hemolysis in whole-blood, was designed using CYTOSEP paper (available from Ahlstrom Filtration, Inc.), which retards red blood cells during capillary draw of blood. The CYTOSEP paper was cut into strips of dimensions 25×5 mm. A drop of a whole-blood sample (about 50 µL), prepared by the method disclosed in Example 1, was placed onto one end of each strip. As the samples containing red blood cells wicked along each strip, the plasma front moved ahead of the red blood cells such that a separation was achieved. By the time the plasma fraction reached the end, red blood cells traversed only about 5–10 mm along the strip. Samples which contained hemolyzed blood exhibited a distinct redness in the plasma fraction as it separated from the red blood cells, whereas those samples that were unhemolyzed did not show a distinct redness, remaining yellowish. All available grades of CYTOSEP were tested, with similar good results. This experiment demonstrated that hemolysis sufficient to result in an elevation of at least 0.1 mM in the potassium concentration is easily visualized.

EXAMPLE 3

The experiment of Example 2 was repeated, except that reagents for colorimetrically detecting the peroxidase activity of hemoglobin were impregnated into the region of the CYTOSEP paper at the end opposite to where the whole-blood sample was added. The reagents included o-toluidine and mixture of tetramethylbenzidine and diisopropylbenzene dihydroperoxide. The reagent-impregnated strips also gave good separation of the serum fraction from red blood cells, and visualization of hemolyzed samples was even clearer than in the strips not containing a chromogenic reagent, due to the development of a blue-green color.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An apparatus for estimating a change in an analyte in a blood sample which is due to the hemolysis of red blood cells comprising:

(a) a dry separation material to which a portion of said blood sample may be applied and a remainder, said material having physical characteristics effective to separate a fraction of said sample by wicking action, which fraction would essentially be free of red blood cells but would contain a representative amount of any extracellular hemoglobin that may be present in said sample;

(b) a location in said remainder providing means for ascertaining the amount of said extracellular hemoglobin in said fraction; and, (c) a correlation means for estimating a change in said analyte in said sample from the amount of said extracellular hemoglobin in said fraction.

2. The apparatus of claim 1 in which said fluid sample is whole-blood.

3. The apparatus of claim 1 in which said correlation means comprises a colored chart displaying at least one color hue of an estimated concentration of extracellular hemoglobin present in a given separated fraction.

4. The apparatus of claim 1 in which said correlation means comprises a chromogenic reagent that reacts with said extracellular hemoglobin to provide a color change.

5. The apparatus of claim 4 which further comprises an orifice for introduction of said sample.

6. The apparatus of claim 1 in which said correlation means is contained in a viewing region that comes into contact with said fraction.

7. The apparatus of claim 1 which is a single-use cartridge.

8. The apparatus of claim 1 in which said sample is separated into a plasma fraction that can be observed through a viewing window, said window substantially excluding from view that portion of the separated sample which contains intact red blood cells.

9. The apparatus of claim 8 in which a colored chart is positioned within view of said window, said colored chart displaying at least one color hue indicative of an estimated concentration of extracellular hemoglobin present in a given plasma fraction.

10. The apparatus of claim 9 in which said color hue correlates to an elevation in the potassium concentration in said plasma fraction by at least 0.1 millimole per liter.

11. The apparatus of claim 9 in which said color hue correlates to an elevation in the potassium concentration in said plasma fraction by at least 0.5 millimole per liter.

12. The apparatus of claim 1, comprising at least two color hues, each of which is indicative of an estimated concentration of extra cellular hemoglobin present in a given plasma fraction.

13. The apparatus of claim 1 wherein the correlating means comprises a color chart.

14. The apparatus of claim 1 wherein the dry separation material further comprises a chromogenic reagent.

15. The apparatus of claim 14, wherein the chromogenic reagent is selected from the group consisting of o-toluidine, diisopropylbenzene dihydroperoxide and tetramethylbenzidine.

16. The apparatus of claim 14 wherein the dry separation material further comprises a quenching agent.

\* \* \* \* \*